United States Patent
Temple

(10) Patent No.: US 8,329,114 B2
(45) Date of Patent: Dec. 11, 2012

(54) DEVICES AND METHODS FOR SAMPLING BIOLOGICAL FLUIDS

(75) Inventor: John Temple, Chelsea, MI (US)

(73) Assignee: Hemobotics, LLC, Grayslake, IL (US)

( * ) Notice: Subject to any disclaimer, the term of this patent is extended or adjusted under 35 U.S.C. 154(b) by 452 days.

(21) Appl. No.: 12/406,815

(22) Filed: Mar. 18, 2009

(65) Prior Publication Data

US 2009/0305407 A1 Dec. 10, 2009

Related U.S. Application Data

(60) Provisional application No. 61/037,587, filed on Mar. 18, 2008.

(51) Int. Cl.
*B01L 3/02* (2006.01)

(52) U.S. Cl. ........ 422/501; 422/504; 422/505; 422/509; 422/512; 422/521; 422/537; 422/540

(58) Field of Classification Search .................. 422/501, 422/504–505, 509, 512, 537, 540, 521; 435/307.1, 435/372
See application file for complete search history.

(56) References Cited

U.S. PATENT DOCUMENTS

| | | | |
|---|---|---|---|
| 5,415,532 A | 5/1995 | Loughnane et al. | |
| 5,577,891 A | 11/1996 | Loughnane et al. | |
| 6,793,828 B2 | 9/2004 | Dolecek et al. | |
| 2005/0019311 A1 | 1/2005 | Holaday et al. | |
| 2005/0281713 A1 | 12/2005 | Hampsch et al. | |
| 2009/0081078 A1* | 3/2009 | Caramuta | ........................ 422/44 |

* cited by examiner

*Primary Examiner* — Brian R Gordon
(74) *Attorney, Agent, or Firm* — Biotech Beach Law Group PC

(57) ABSTRACT

Devices, instruments, systems and methods are provided in which a primary line that receives a biological fluid is selectively sampled by a plurality of collection chambers. Selective sampling occurs by selectively accessing the primary line and selective engagement of a sampling pump under control of a microprocessor. Further, the instrument housing reversibly houses a drive assembly and sample collection housing to permit the interchangeability of drive assemblies and collection housings and thus enhance sterility or reduction of cost.

15 Claims, 16 Drawing Sheets

DEVICES AND METHODS FOR SAMPLING BIOLOGICAL FLUIDS

CROSS REFERENCE TO RELATED APPLICATIONS

The present invention claims benefit of priority to U.S. patent application Ser. No. 61/037,587, entitled, Portable, Automatic Blood Sampling System and Method, filed on Mar. 18, 2008; the contents of which are incorporated herein by reference in their entirety.

TECHNICAL FIELD

The present invention relates generally to devices and methods for sampling of biological fluids and more particularly to a portable, automated blood sampling device, system and its method of use.

BACKGROUND OF THE INVENTION

Sampling of biological fluids is an important process for determining the presence of bacteria, hormones, parasites, toxins, analytes as well as the metabolism of drugs and other substances. Often, sampling is performed manually or on an as-needed basis. For example, in laboratory settings animals are frequently anesthetized followed by sample collection using manually operated syringes or manually inserted blood collection tubes. Similarly, in humans blood is frequently drawn using syringes or blood collection tubes, often provided with anticoagulants.

Given that traditional methods are labor intensive and time-consuming, automated sampling systems have been devised, some of which are for sale commercially. DiLab, Inc. (Littleton, Mass.), Instech Solomon (Plymouth Meeting, Pa. USA) and Red Box Direct Limited (Dublin, Ireland) may be among those offering units for sale.

However, there are various deficiencies in current systems. Among these include systems that are difficult to use and lack desired portability. In laboratory settings, many use heavy or bulky components, requiring that the animal be tethered to the apparatus, typically through a swivel joint to facilitate greater mobility. Still others suffer from difficulty in cleaning and others use sample collection methods that may cause contamination between samples. Thus the need remains for an automated sampling system that is portable, efficient and may be provided in a sterile form.

SUMMARY OF THE INVENTION

The present invention addresses deficiencies in current sampling devices and methods and provides related benefits. In one aspect of the present invention an instrument for sampling biological fluids is provided, including a primary line having an inlet for receiving a biological fluid; a fluid reservoir for storing an anticoagulant or rinsing fluid; a waste container; and a plurality of sample collection chambers attached to a plurality of collection lines for selectively collecting fluid samples. Sample collection, rinsing of lines and collection of waste occurs through the use of at least one pump and a selecting valve. The pump selectively pumps each of: fluid from the primary line to the waste container, fluid from the primary line to each of the sample collection chambers independently and fluid from the fluid reservoir to the primary line. The selecting valve, such as a three way valve selectively permits access between each of: the primary line and waste container, the fluid reservoir and primary line, and optionally the fluid reservoir and waste container. The instrument is controlled by a microprocessor operably linked to memory and a power source, which allows selective control over pumping and valve operations such that each is provided in correct series or as programmed.

In some embodiments, each collection line also includes a terminal needle for selectively piercing the primary line to access the central cavity. Thus piercing permits the sample collection line to fluidly communicate with the primary line and thus deliver biological sample to the collection chamber during pumping. The primary line may be pierced prior to or concurrently while driving the pump. When not in use, the terminal needle is primarily housed within the wall of the primary line.

In further embodiments, the temperature of the collection chamber is regulated by a cooling element, such as a peltier cooling element, optionally coupled to a substrate for cooling assistance. In still further embodiments a thermosistor is provided to initiate or regulate cooling. Each chamber may have its own assigned cooling element or a single cooling element may cool multiple chambers.

In still further embodiments, an external control unit is provided for receiving instructions from a user and transmitting operative programming to the microprocessor according to instructions. In still further embodiments the microprocessor returns data or instructions to the external control unit, such as instrument status, sample collection information, temperature information, battery level and sample collection time remaining.

In another aspect of the present invention a drive assembly with collection chambers for sampling biological fluids is provided that is attachable to and removable from a series of motors for operation. The drive assembly includes a primary line having an inlet end for receiving a biological fluid; a fluid reservoir for storing an anticoagulant or rinsing fluid; a waste container for storing waste; a plurality of sample collection chambers attached to a plurality of collection lines for selectively collecting a plurality of fluid samples from the primary line; a peristaltic pump including a plurality of rotor housings capable of selective engagement with a central rotor; and a cam assembly including a rotatable cam, positionable along the plurality of rotor housings such that rotation between two positions results in selective engagement or disengagement and optionally piercing of the primary line. The device may also include a selecting valve for selective communication between the primary line and the fluid reservoir, the primary line and the waste container, or the fluid reservoir and the waste container.

Each of the rotor housings may be assigned to one of the following: the fluid reservoir, the waste container or one of the collection chambers. Engagement of any of the rotor housings with the central rotor results in compression of flexible tubing, which is positioned along an inner perimeter of the rotor housing; thus permitting peristaltic pumping. Further, when a rotor housing associated with a collection chamber is engaged, the rotor housing drives a needle into the cavity of the primary line, which permits fluid communication and facilitates pumping of the biological fluid. When not engaged, the needle is generally positioned within the wall of the primary line. In still further embodiments, springs contacting the rotor housings, are compressed when the cam is in the first position and decompressed when in the second position thus assisting with disengagement of the rotor housing with the central rotor when not selected.

In instances where the biological fluid is blood, a cooling element, which may include one or more pettier cooling elements may contact or cool the sample collection chambers thus cooling the samples. In some embodiments, each of the plurality of collection chambers includes at least one peltier cooling element. In other embodiments, two or more sample collection chambers share a cooling element. In still further embodiments a thermosistor is provided, which detects the presence of fluid in the primary line, a collection line or a sample collection chamber. In still further embodiments, detection of fluid by the thermosistor activates at least one cooling element.

In some embodiments the drive assembly includes a threaded positioning rod complementary to a threaded aperture extending through the cam assembly. Rotation of the threaded positioning rod, such as by a motor under control of a microprocessor, can horizontally position the cam assembly across and above the plurality of rotor housings. In further embodiments, the device includes a rotating shaft slidably inserted through the cam such that rotation of the shaft rotates the cam into the first and second positions, which selectively engage and disengage the rotor housing and central rotor.

In another aspect of the invention, an instrument for sampling a biological fluid is provided, which includes a drive assembly as disclosed herein that is reversibly attachable to an instrument housing, which permanently houses a series of motors and a microprocessor. In these embodiments, the drive assembly selectively attaches to the instrument housing such that a pump motor may rotate the central rotor; a positioning motor may position the cam assembly; and a cam motor may rotate the cam between first and second positions, such as by rotating a slidably inserted rod. Each are under control of a microprocessor operably linked to memory and a power source. In further embodiments the selecting valve is actuated by a valve motor, optionally using a valve stem or rod. In still further embodiments, sample collection chambers are positioned within a collection housing that is reversibly attachable to the drive assembly and together or independently are removable from the instrument housing.

The microprocessor instructs operation of the pump motor, positioning motor, cam motor and valve motor as needed. Instructions provided by the user via an external control unit may be received by the microprocessor, stored in memory and accessed according to particular programs or operations.

Additional advantageous features of the instrument include a removable drive assembly and removable sample collection housing which allows the substitution of multiple drive assemblies and collection housings with the instrument. Thus drive assemblies and/or collection housings may be provided separately and optionally packaged in a sterile packaging to reduce contamination. In some embodiments, the instrument housing also includes electrical connectors for one or more cooling elements such that when the drive assembly and collection housing is inserted, collection chambers may be cooled. Each cooling element may contact one of the collection chambers or may share collection chambers. Regulation or activation of cooling elements may at least in part involve a signal generated from a thermosistor.

In another aspect of the present invention a system for sampling a biological fluid is provided, which includes at least one of the devices or instruments provided herein and an external control unit operably linked to the microprocessor. The external control unit may include a computer system including a software program, in which the software program accepts entry of data from a user, such as data corresponding to sample volume for collection, the number of sample volumes to be collected and the like. The external control unit may determine the order of sample collection and/or rinsing operations and may transfer the order as instructions to the microprocessor for performance. Further, the microprocessor may transmit data to the external control unit such as graphical, numerical data and the like corresponding to the sample collection process or status. The microprocessor may control the timing of sample collection including sampling time, rinsing time or priming time. The microprocessor may adjust the speed of pumping, or movement of each motored element as needed and may be adjusted in response to one or more sensors of an event.

In another aspect of the present invention a method of sampling a biological fluid is provided including providing an instrument provided herein, connecting the instrument or assembly to the subject in need of collection and collecting a series of samples. In further embodiments, samples are collected according to instructions received from an external control unit, which is programmable by a user.

BRIEF DESCRIPTION OF THE DRAWINGS

FIG. 2A depicts the plurality of collection lines 28 having needles 30 initially positioned within the wall 48 of the primary line 12. FIG. 2B depicts fluid flow into the primary line 12, through the selecting valve 24 and into the waste reservoir 20. FIG. 2C depicts the selective positioning of a first needle 30a within the cavity 50 of the primary line 12 thus permitting pumping or collection of the sample into the first collection chamber 26a where it may optionally be cooled by the cooling element 44. FIG. 2D depicts the anti-coagulant or rinsing solution delivered from the fluid reservoir 16, through the selecting valve 24 and into the primary line 12.

FIG. 11B demonstrates a plurality of needle housings 94 joined as a single unit for attachment with the housing 90, such as at the tops 95.

DETAILED DESCRIPTION OF THE INVENTION

Figure 1A:
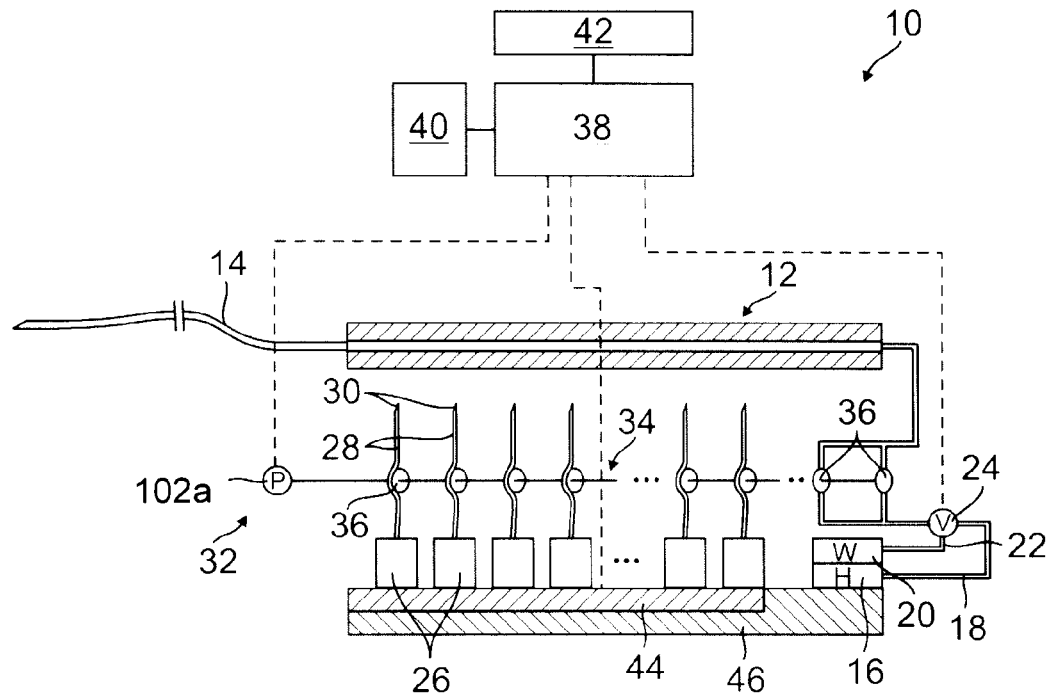
FIG. 1A provides a schematic diagram depicting an overview of various features of the device 10. A primary line 12 having an inlet end 14 for fluid connection with a subject, such as a medical patient or laboratory animal, is coupled to a fluid reservoir 16, which stores an anticoagulant or rinsing fluid, via a reservoir line 18. The primary line 12 is also coupled to a waste container 20 via a waste line 22. Between the reservoir line 18 and waste line 22 is a selecting valve 24 which selectively permits access between the fluid reservoir 16 or waste container 20 with the primary line 12. A plurality of sample collection chambers 26 selectively accesses the primary line 12 through a plurality of collection lines 28 and needles 30. A peristaltic pump 32 including a central rotor 34 including a plurality of wipers 36 selectively delivers fluid between the primary line 12 and the fluid reservoir 16 and between the waste container 20 and sample collection chambers 26. Operation is controlled through a microprocessor 38 operatively connected to memory 40 and a human interface 42. The microprocessor 38 instructs operation of the pump motor 102a and selecting valve 24. Also shown is a cooling element 44 and insulation 46 to cool and insulate the collection chambers 26.

The present invention provides devices, systems and methods for the collection of biological samples from a subject. The device will have particular utility for the collection of biological fluids, such as blood. The present device and system may be used with human patients such as to monitor therapies, assist in medical diagnosis and the like and may be used with experimental animals to advance medical research.

It is an object of the present invention to provide a device 10 that includes a removable or disposable sampling drive assembly 60 that is interchangeable or detachable from an instrument housing 100. Removal of the drive assembly 60 from the instrument housing 100 disconnects the drive assembly 60 from motors 102, microprocessor 38, memory 40, transmitter, receiver and the like. As such, the sampling drive assembly 60 may be discarded after use without discarding the instrument housing 100 and many reusable electrical components. Thus a new drive assembly 60 may be used for each collection event or experiment, which reduces contamination and variation in sampling. Further, the replaceable drive assembly 60 may decrease expenses associated with construction of entire instrument systems themselves and the like while providing efficient sampling of a subject's biological fluid. In addition a sample collection housing 90, which houses sample collection chambers 26, is detachable from the drive assembly 60 and removable from the instrument housing 100, which also assists in the interchangeability and replacement of various components, while retaining reusable components with the instrument housing 100.

Figure 1B:
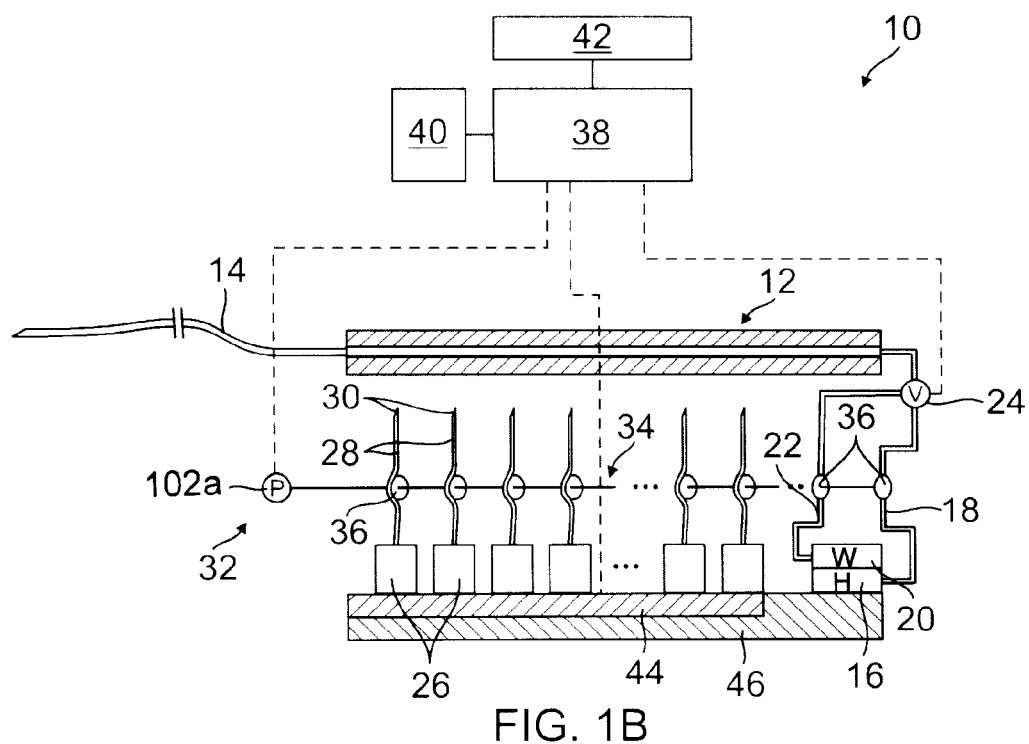
FIG. 1B depicts an alternative positioning of the selecting valve 24 with respect to the primary line 12 and central rotor 34.

An overview of operative features of the device is provided in FIGS. 1A-B, which provides a primary line 12 including an inlet end 14 through which blood or biological sample is received from the subject requiring sampling. The primary line 12 may retrieve fluids from the subject using any suitable means such as a catheter, which may access a vein, artery, capillary and the like as known in the present art for the collection of a biological fluid such as a blood sample, a urine sample and the like. The primary line 12 selectively communicates with a fluid reservoir 16, which houses an anticoagulant or rinsing fluid; a waste container 20 for collecting waste; and a plurality of sample collection chambers 26.

Figure 2A:
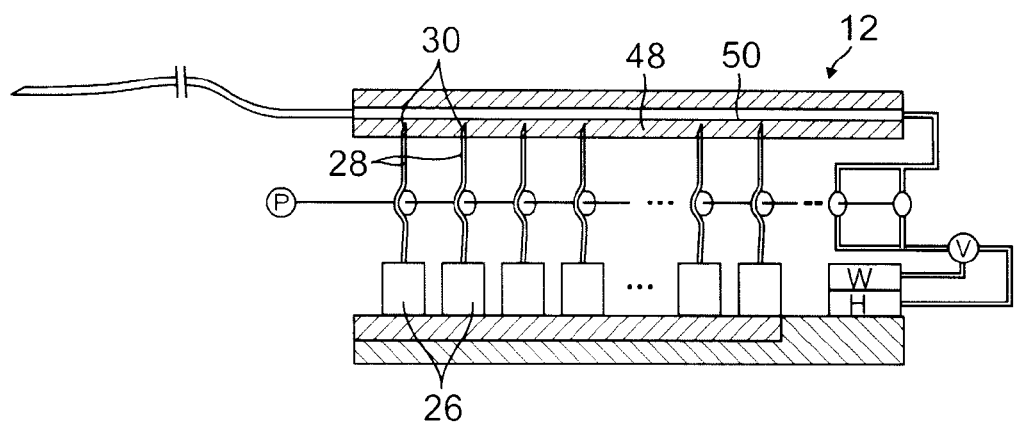
FIGS. 2A-D are schematic diagrams depicting exemplary operative steps performed through the primary line 12.
Figure 2B:
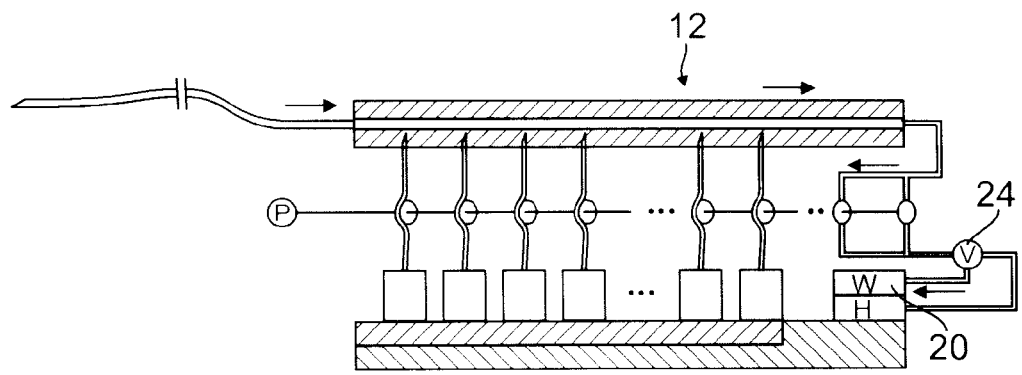
Figure 2C:
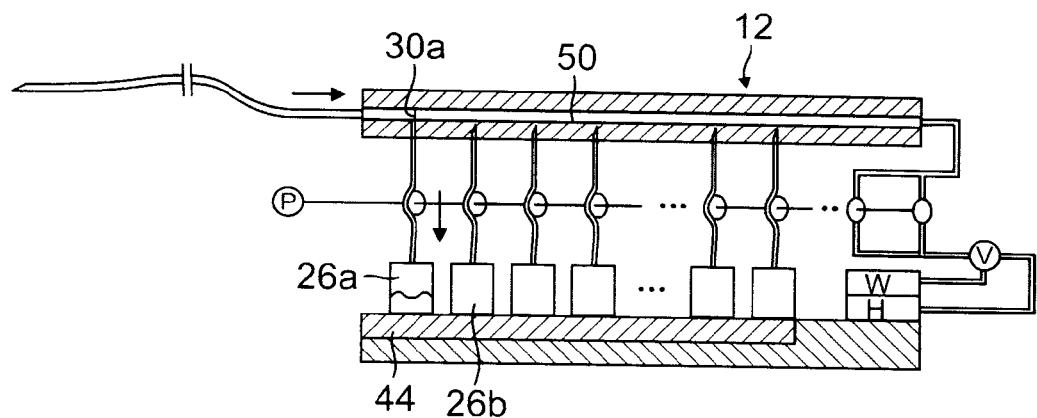
Figure 2D:
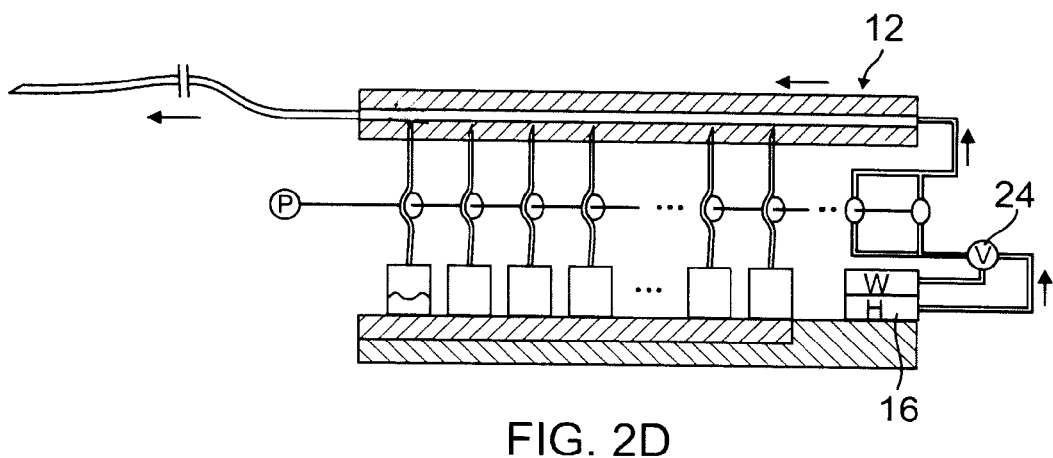

An overview of an exemplary procedure or method is provided in FIGS. 2A-D. An initial setting is provided in FIG. 2A, in which the needles 30 are each positioned within the wall 48 of the primary line 12. FIG. 2B depicts priming the primary line 12 or receiving sample by pumping the sample through the primary line 12 and into the waste container 20. Once the system is primed, a needle 30 accesses the cavity 50 of the primary line 12 and fluid is pumped then collected in the first collection chamber 26a as shown in FIG. 2C. After which, the anticoagulant is pumped into the primary line 12 to rinse and/or prevent clotting as depicted in FIG. 2D. The fluid can again be received and collected as depicted in FIGS. 2B and 2C using the next collection chamber 26b, then rinsed as in FIG. 2D and repeated as desired.

While the primary line 12 may be constructed from any suitable material known in the medical device or polymer arts, such as polypropylene, latex, silicone, plastic polymers and the like, a self-sealing polymer may be desirable when needles 30 are repositioned or recessed into the wall 48 of the primary line 12 after sample collection. Further, although the diameter of the primary line 12 is nonlimiting, in preferred embodiments, the wall 48 of the primary line should be sufficiently thick to retain an aperture of the needle 30 when positioned within the wall 48. Further, the inner diameter of the primary line 12, which defines a cavity 50, should be sufficiently large to permit sufficient access to the cavity 50 by the needle 30 to obtain blood samples. In embodiments where the needle 30 is a non-coring needle, such as us but not limited to Huber needle, preferably the inner diameter of the primary line 12 and thus cavity 50 is greater than the lumen of the non-coring needle, most preferably slightly larger than the lumen of the non-coring needle. The diameter and thickness of the primary line 12 may be altered or optimized according to the desires of the user. Preferably, the volume of the cavity 50 is known such that the amount of desired anticoagulant or rinsing solution can be determined to prevent excess delivery into the subject.

Figure 14A:
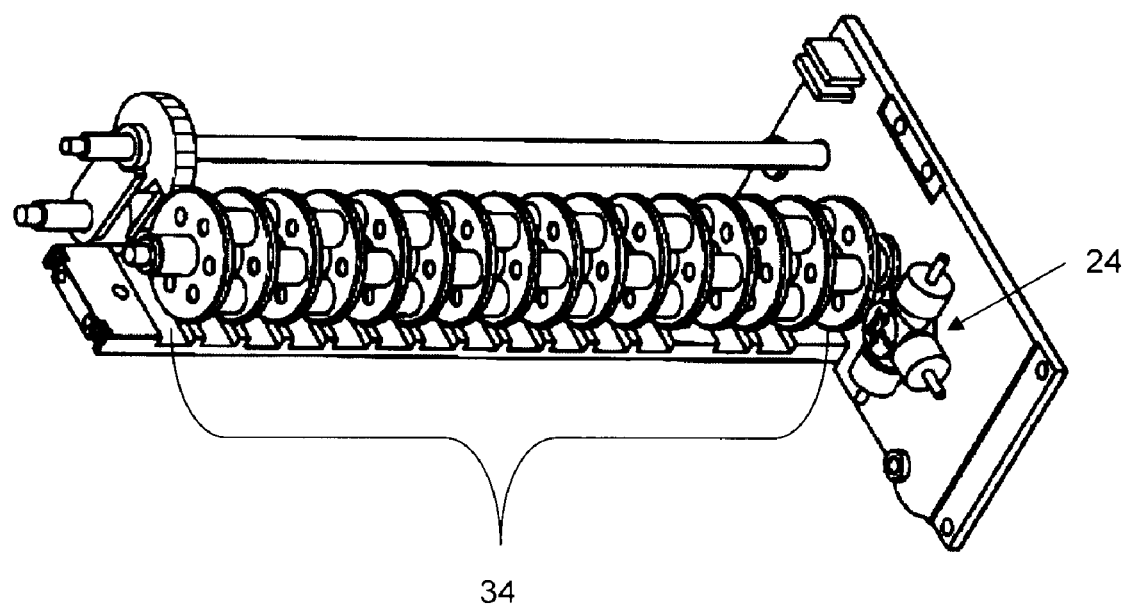
FIGS. 14A-B depict a central rotor 34 for multiple sample collection and also depicts a preferred positioning of the selecting valve 24.
Figure 14B:
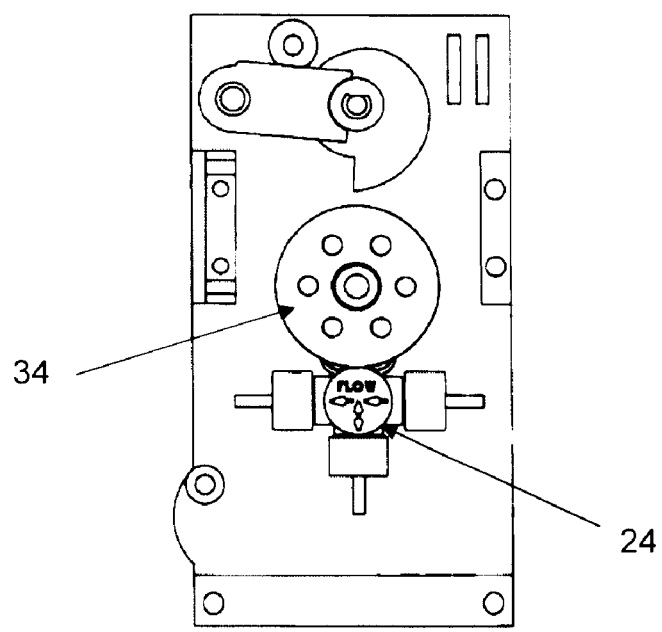

Access between the primary line 12, fluid reservoir 16 and waste container 20 is selected by the selecting valve 24, which is preferably a valve providing three-way selection. An exemplary selecting valve 24 is shown in FIGS. 14A-B. In an exemplary embodiment, a first selection fluidly communicates a waste container 20 with the primary line 12 as depicted in FIG. 2B, and a second selection fluidly communicates the fluid reservoir 16 with the primary line 12 as depicted in FIG. 2D. A third selection may provide a closed configuration or may permit communication between the fluid reservoir 16 and the waste container 20, such as to prevent blood clotting within the waste line 22. A variety of valves may accomplish these functions. Among these include disk valves, ball and rotor valves and the like. In some embodiments rotation of a valve stem selectively positions a ball and rotor or disk to fluidly connect desired routes via valve ports. Further, depending on the desired configuration, three-way valves, four-way valves and the like may be chosen. One skilled in the present art will recognize that the selecting valve may be actuated according to a variety of known methodologies. In some embodiments, the valve is operatively connected to a valve motor 102d, wherein a motor rotates a spindle to control direction or flow among valve ports which join the primary line 12, reservoir line 18, waste line 22 and the like. In some embodiments, the valve is an electromechanical valve. Many electromechanical valves are known in the art and typically include an electric motor or solenoid combined with an actuator. In further embodiments, the actuator is controlled by liquid or air pressure, such through vacuum and the like. In preferred embodiments, the selecting valve 24 is controlled by instructions provided by the microprocessor 38.

In preferred embodiments, the fluid container 16 contains an anticoagulant or rinsing solution. Such solutions may be added by the user, such as through an access aperture or valve that accesses the fluid reservoir 16 and the like. Alternatively, the anticoagulant or rinsing solution may be initially provided within the fluid reservoir 16 in a disposable drive assembly 60. The anticoagulant is a substance that prevents coagulation. That is, a substance that stops blood from clotting. The anticoagulant may be selected from a variety of anticoagulants known in the present art, such as but not limited to heparin, heparin derivatives, lithium heparin, ethylene diamine tetraacetic acid (EDTA) and the like. The choice of which to use may be determined by users of the instant device 10 in view of later testing procedures or assays. Rinsing fluids may include sodium chloride, phosphate buffered saline (PBS), borate buffered saline (BBS) and the like. In addition, preservatives may also be added as known in the art.

The fluid reservoir 16 delivers the anticoagulant or rinsing solution to the primary line 12 via the fluid reservoir line 18 and selecting valve 24, which is selected to permit flow. Positioning of the fluid reservoir 16 may be varied depending on the desires of the user such as affixed to the drive assembly 60, within the collection housing 60, separately and the like. In preferred embodiments, a peristaltic pump 32 provides the pumping force for delivery. In alternative embodiments a syringe is used to displace anticoagulant or rinsing solution such as by coupling the syringe plunger to a threaded rod and controlling rotation of the rod and thus displacement. Other embodiments include the manual operation of a syringe. The amount of anticoagulant or rinsing fluid delivered may vary depending on a variety of factors, such as the volume of the primary line 12, the concentration of the anticoagulant and the like. In some embodiments 1-1000 microliters ($\mu$L) are delivered. In some embodiments, 1-10 milliliters (mL) are delivered. In other embodiments 10-50 mL are delivered. Such volumes are typically preprogrammed into memory 40 or selected in the form of an option during setup according to the particular needs of the user. The anticoagulant or rinsing solutions may be delivered during any number of desired time points, such as prior to the initial blood draw, after the initial blood draw and prior to the collection of samples, between each or any of the sample collections and the like. Such time periods may be preprogrammed, selected from options during initial setup of the device 10 and the like. In some embodiments a one way valve is positioned between the selecting valve and the fluid reservoir to prevent fluid flow from the primary line 12 into the fluid reservoir 16.

Figure 15A:
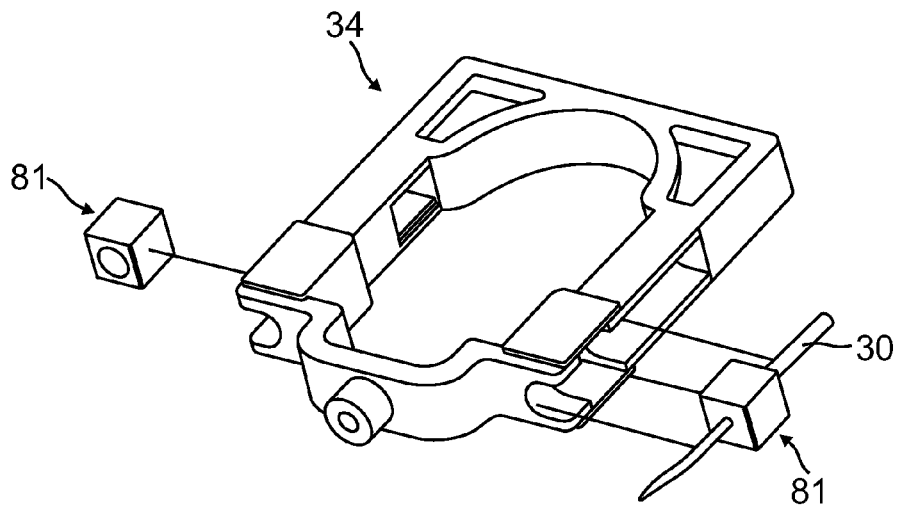
FIGS. 15A-B depict rotor housings 68 that may include sliding guides 81 including the needle 30 for sample collection as shown in FIG. 15A or opposing through bores 79a-b as shown in FIG. 15B.
Figure 15B:
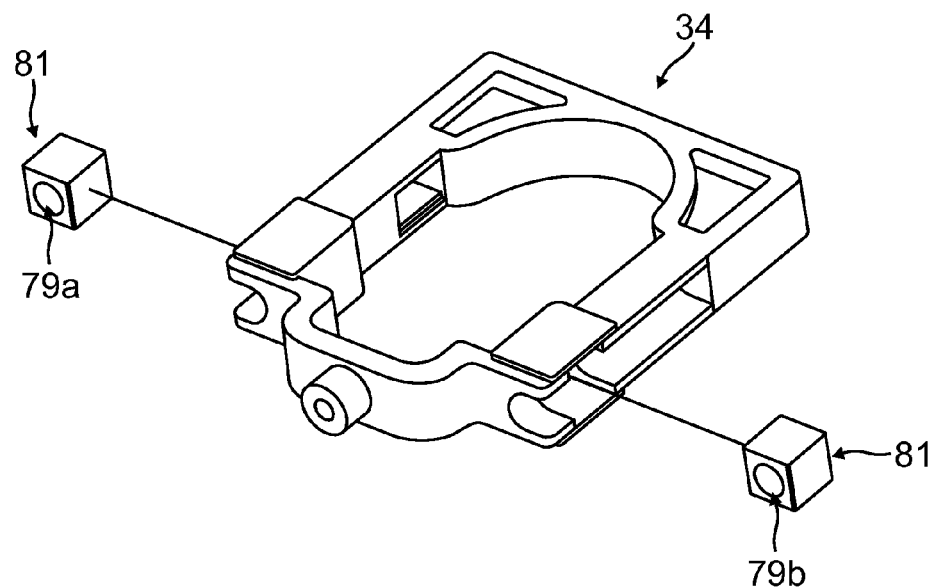

The waste container 20 may be used to collect any fluid not desired for collection into the sample collection chambers 26. As such, the waste container 20 is nonlimiting with respect to volume as the collection volumes may vary significantly depending on the particular patient or subject, volume of blood drawn, the amount of anticoagulant or rinsing solution pumped and the like. Positioning of the waste container 20 may be varied depending on the desires of the user such as affixed to the drive assembly 60, within the collection housing 60, separately and the like. In the preferred embodiment, the waste container 20 includes a waste line 22 connected to selecting valve 24, which is fluidly connected to the primary line 12. In preferred embodiments, the waste line 22 is positioned along a rotor housing 68 such that engagement of the rotor housing 68 with the central rotor 34 induces pumping. An exemplary rotor housing 68 configuration is shown in FIG. 15B which includes opposing through bores 79a-b instead of a needle 30 as depicted in FIG. 15A. In other embodiments, a syringe is used to draw blood or fluid into the waste container 20. In some embodiments a one way valve is positioned between the selecting valve and waste container to substantially prevent waste from exiting the waste container 20. Some users may desire to permit blood flow into the waste container 20 during collection to further facilitate fluid flow for collection.

Figure 8:
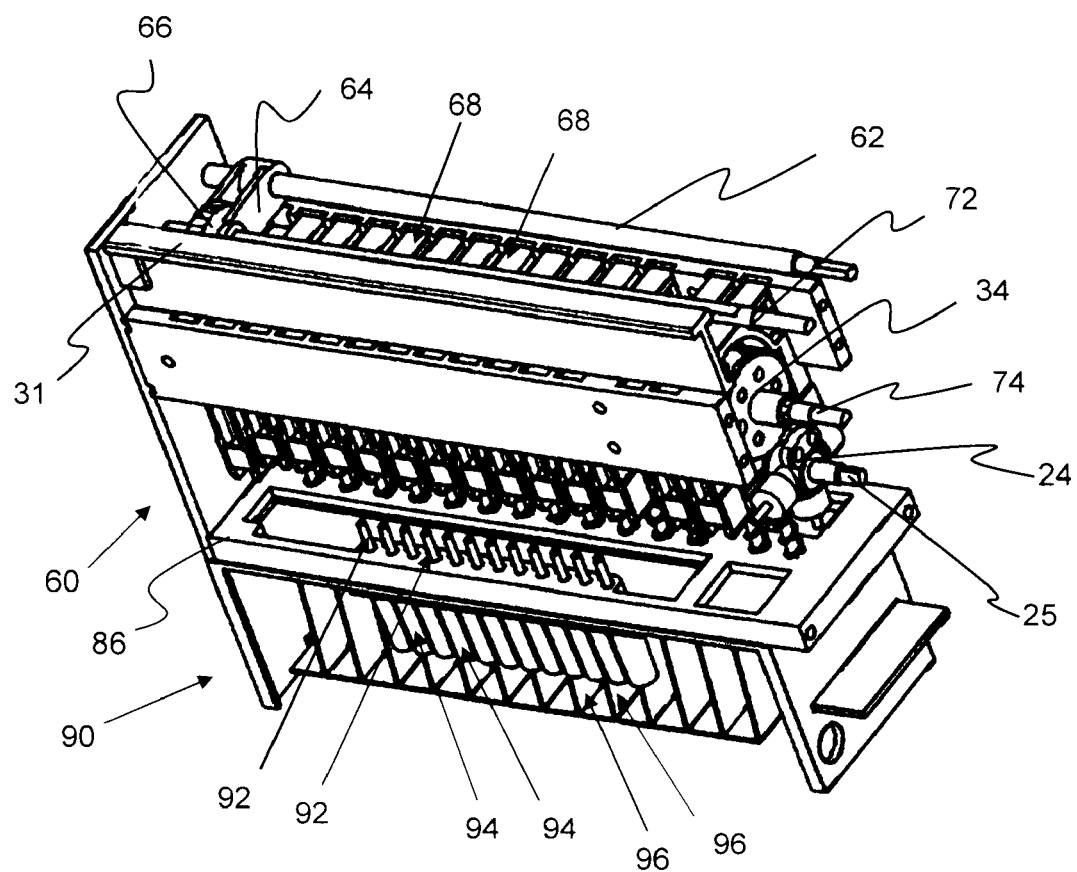
FIG. 8 depicts an exemplary drive assembly 60 attached to a detachable collection housing 90. Penetrating into the detachable collection housing 90 from a drive base 86 are a plurality of collection needles 92 that reversibly engage a plurality of needle housings 94 which project into a collection chamber spacing 96. The selecting valve 24 including a selecting rod 25 is also shown. A needle loading structure 31 is also depicted as well as the cam assembly 64 including rotatable cam 66, positioning rod 62, cam rod 72, rotor housings 68, central rotor 34 and rotor rod 74.

Preferably, blood samples are collected by instructing insertion of a collection needle 30 into the cavity 50 of the primary line 12 and selectively pumping blood into the sample collection chamber 26. Although initially, a needle loading structure 31, such as shown in FIG. 8, may load needles 30 into the wall of the primary line 12. The number of sample collection chambers 26 may vary depending on the needs of the user. In some embodiments the device 10 includes two sample collection chambers 26. In some embodiments the device 10 includes three or more sample collection chambers 26, such as four, five, six, eight, ten, twelve and the like. Thus, a plurality of sample collection chambers 26 may be provided and is thus nonlimiting. Collection chambers 26 may be arranged in any desired configuration and may be selected in series such that a first chamber 26a collects a first sample, a second chamber 26b collects a second sample, and the like. Between sample collections, the primary line 12 may be rinsed with anticoagulant as programmed by the user, in response to a sensor, which senses the need for rinsing, or as preprogrammed. Thus a plurality of samples may be collected, such as two, three, four, five, seven, nine, twelve, twenty four, and the like as needed with desired rinsing and waste collection.

Figure 6A:
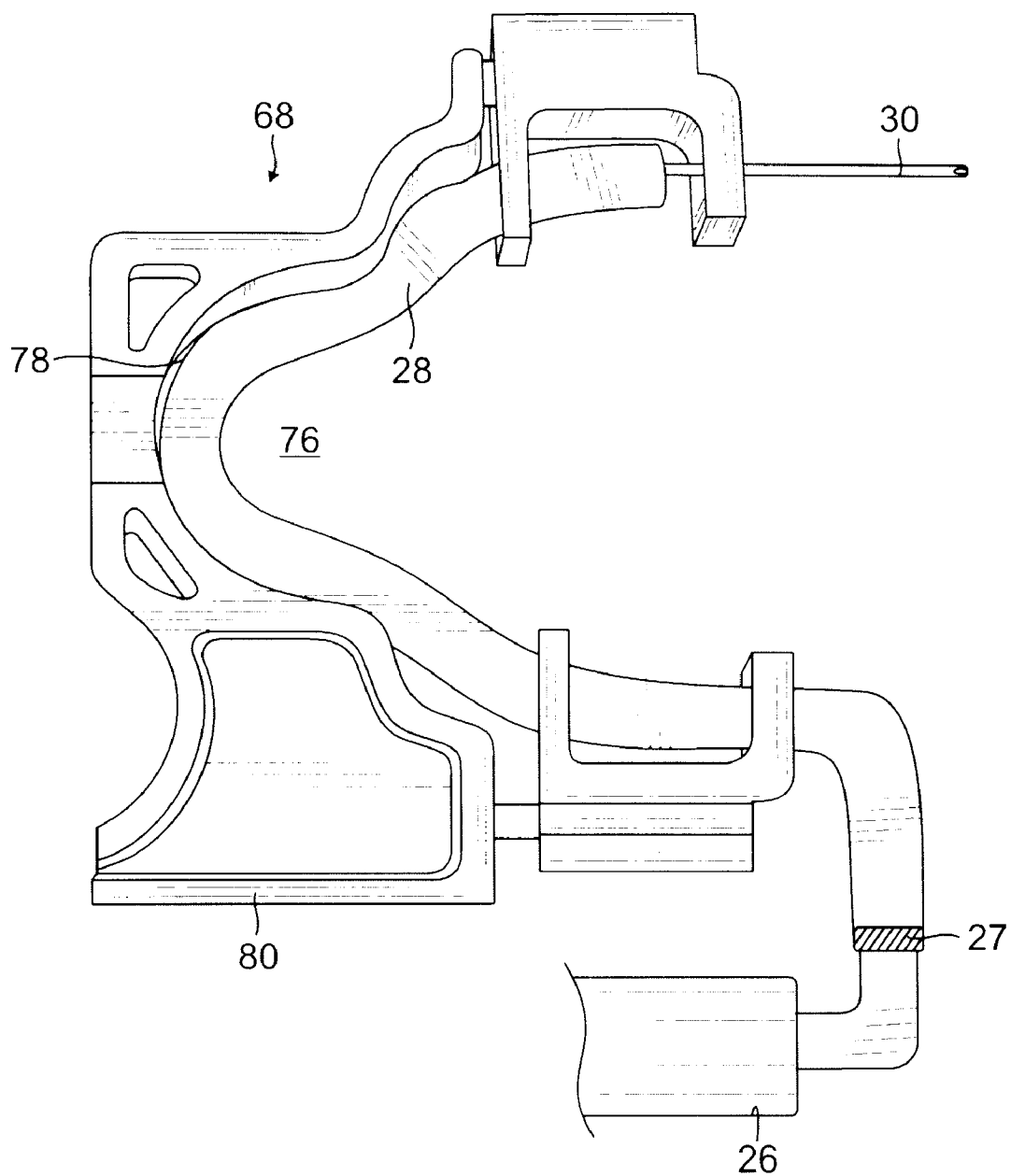
FIG. 6A depicts an exemplary rotor housing 68 having a rotor cavity 76 with a sample collection line 28 with needle 30 and connected to a collection chamber 26 after passing a thermosistor 27. The sample collection line 28 is positioned along the inner perimeter 78 of the rotor housing 68. A rotor housing tongue 80 is also shown.

Operationally, in a preferred embodiment, each sample collection chamber 26 is fluidly connected to a flexible sample collection line 28 which threads along the inner perimeter 78 or circumference of a rotor housing 68 substantially as shown in FIG. 6A. Collection is permitted by piercing a needle 30, such as a non-coring or Huber needle, into the cavity 50 of the primary line 12. Sample collection follows by rotation of the central rotor 34, such as by a pump motor 102a, against the engaged rotor housing 68, which compresses the sample collection line 28 in a peristaltic fashion. Rotation and/or engagement may continue until a desired volume is obtained, a desired time point is reached and the like. One skilled in the art will recognize the desired collection volume may vary widely depending on the needs of the user. For instance, a small volume may be collected when providing a small volume for a highly a sensitive measurement technique such as polymerase chain reaction (PCR), which exponentially amplifies target sequences. However, when detecting a dilute analyte greater volumes may be desired.

Once the sample is collected, the engaged rotor housing 68 may disengage from the central rotor 34 and the needle 30 may be removed from the cavity 50 of the primary line 12 and return into the wall 48 of the primary line 12; thus reducing or blocking access to the sample collection chamber 26. Disengagement may be assisted by permitting the decompression of a compressed spring 70 positioned against the rotor housing 68. In some instances, blood within the collection line 28 is encouraged or permitted to clot after collection is complete to assist in preventing further collection.

Fluids may also be collected or delivered using alternative pump configurations and structures. In some embodiments the primary line 12 is accessed by collection lines 28 and squiggle motors selectively deliver the biological sample to collection chambers 26. Squiggle motors are piezoelectric motors that change in shape when electrically excited. Ultrasonic vibrations caused by delivering power to an actuator causes a rotational nut to vibrate in an orbit. Thus, selective activation or control of a plurality of squiggle motors by the microprocessor 38 can selectively pump biological fluid into collection chambers 26, into a waste container 20 or from a fluid reservoir 16.

In some embodiments, the sample collection chamber 26 itself is provided as a collection tube, vial or bag joined to the sample collection line 28, whether or not reversibly joined, such as through complimentary luer locks. However, in preferred embodiments, the sample collection chamber 26 is associated with a temperature controlled collection housing 90, which may be removable from the drive assembly 60. In some instances, the sample collection lines 28 are reversibly attachable along their length for selective removal of the sample collection chambers 26 or collection housing 90 from the drive assembly 60.

Figure 7:
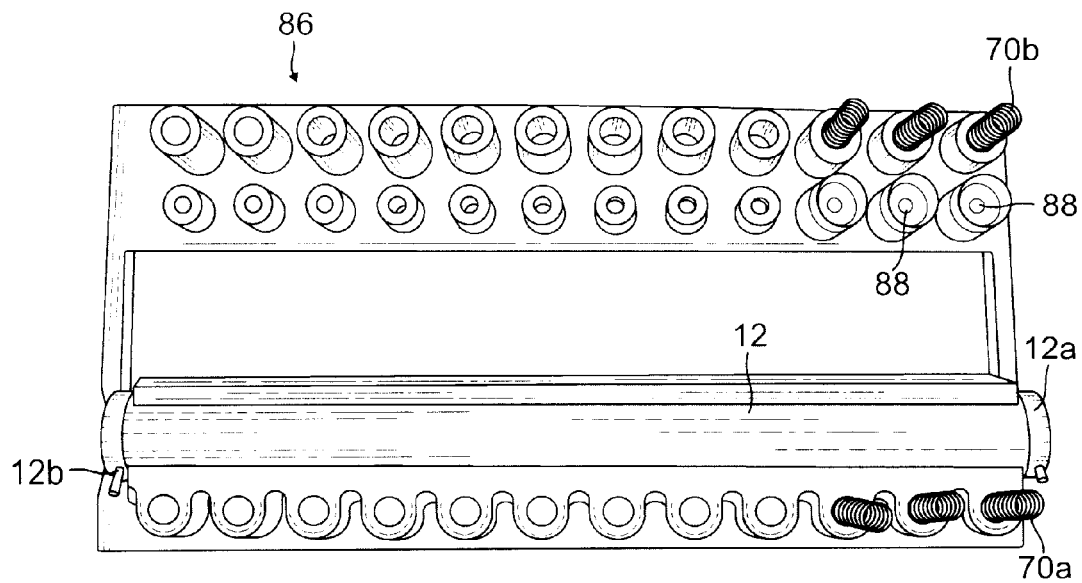
FIG. 7 depicts an exemplary drive base 86 showing the primary line 12 with opposing end connectors 12a-b, opposing springs 70a-b and a plurality of collection throughways 88.
Figure 9:
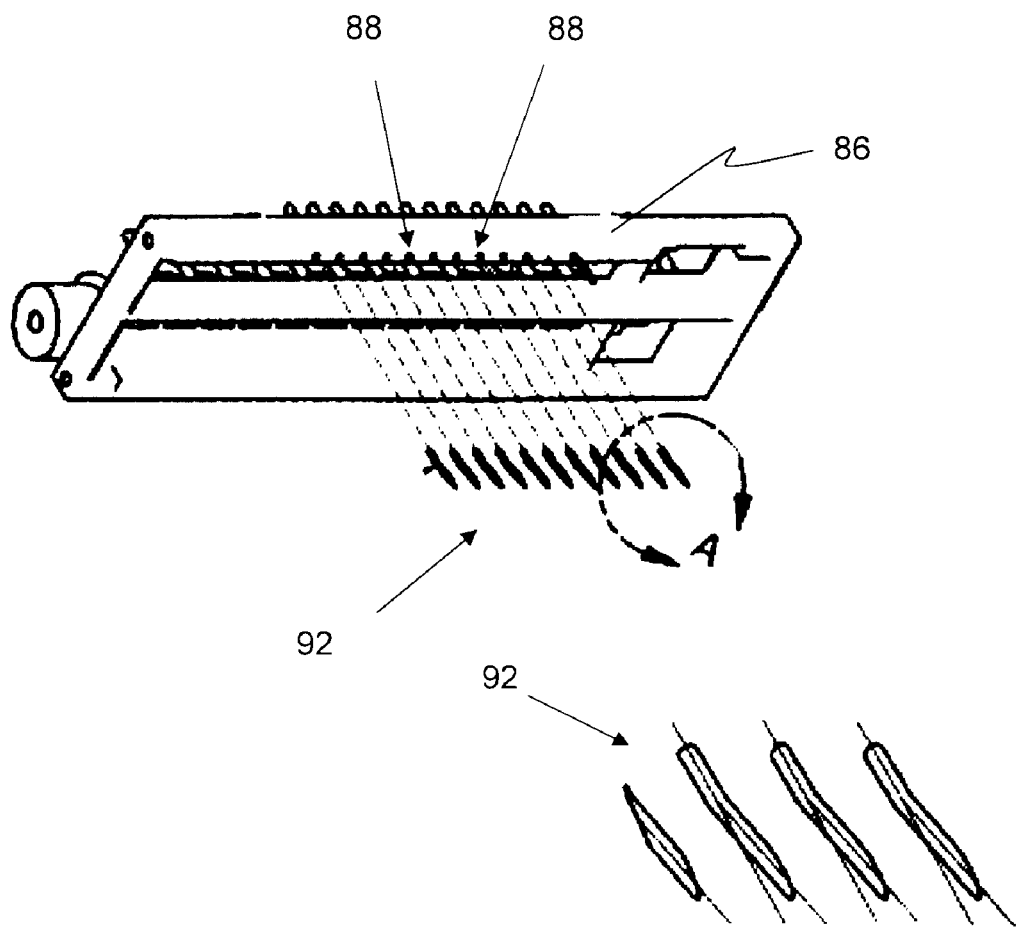
FIG. 9 depicts the insertion the collection needles 92 into the collection throughways 88 of an exemplary drive base 86.
Figure 10:
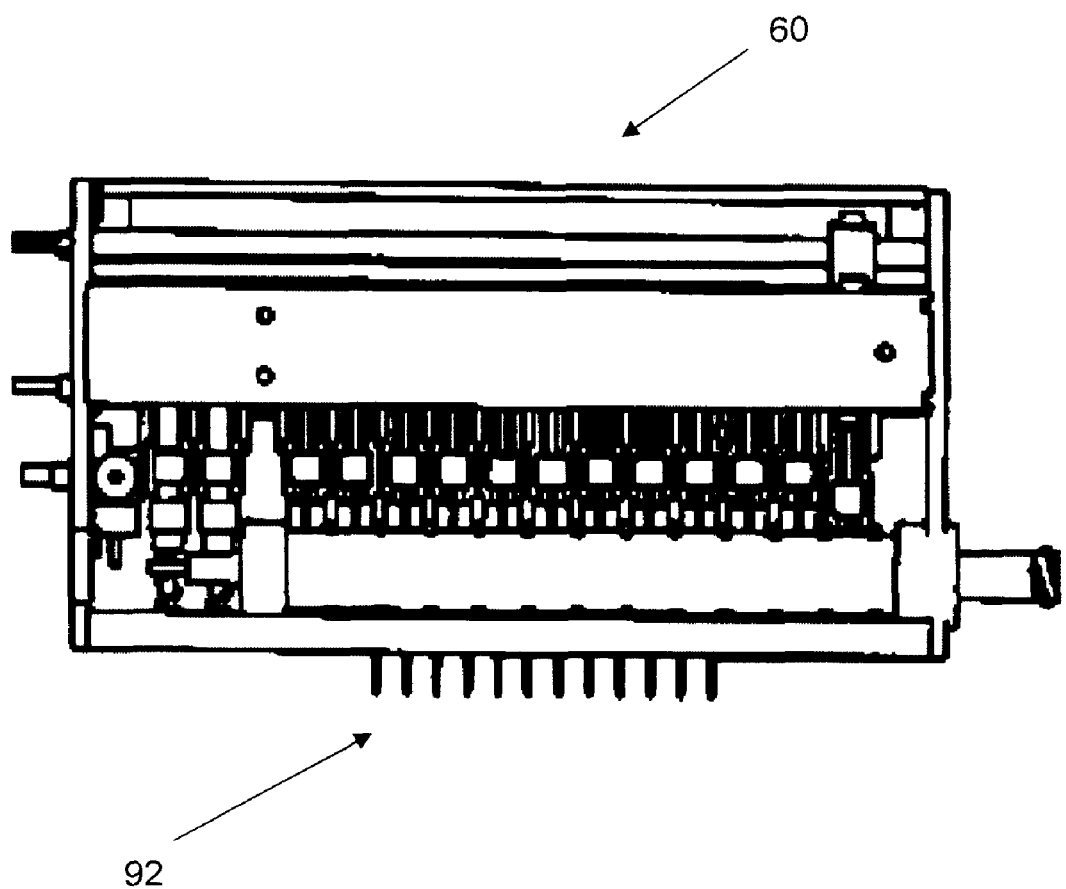
FIG. 10 depicts a drive assembly 60 with inserted collection needles 92.
Figure 11A:
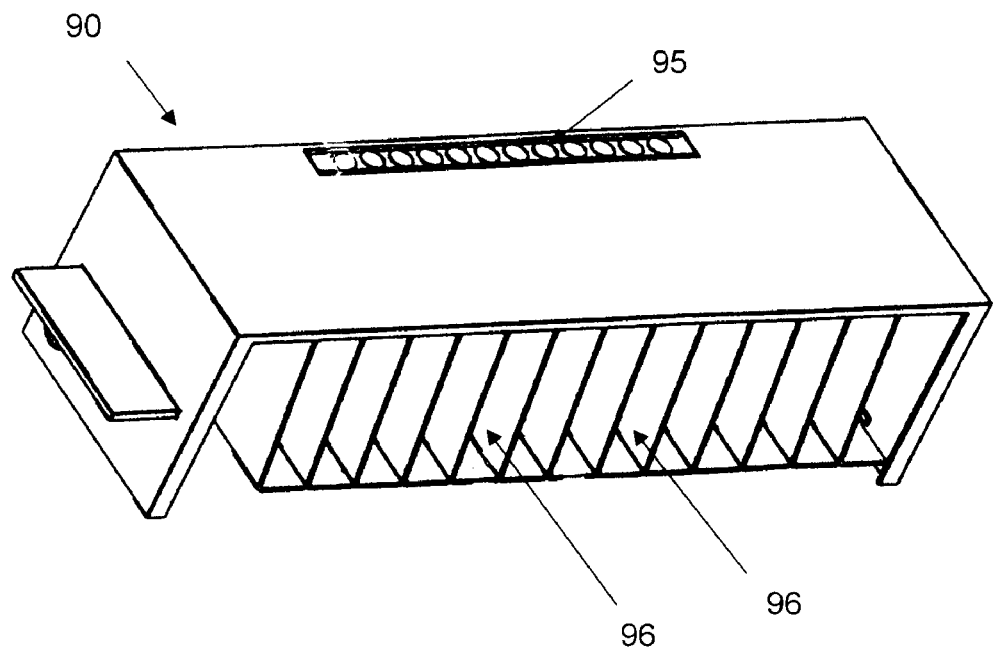
FIGS. 11A and 11B depict opposing views of a detached collection housing 90.
Figure 11B:
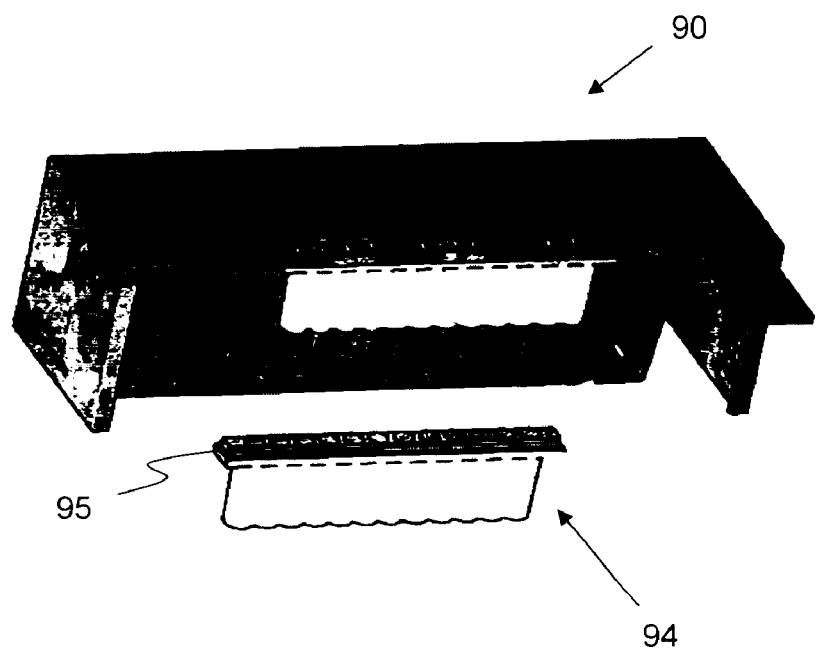
Figure 12:
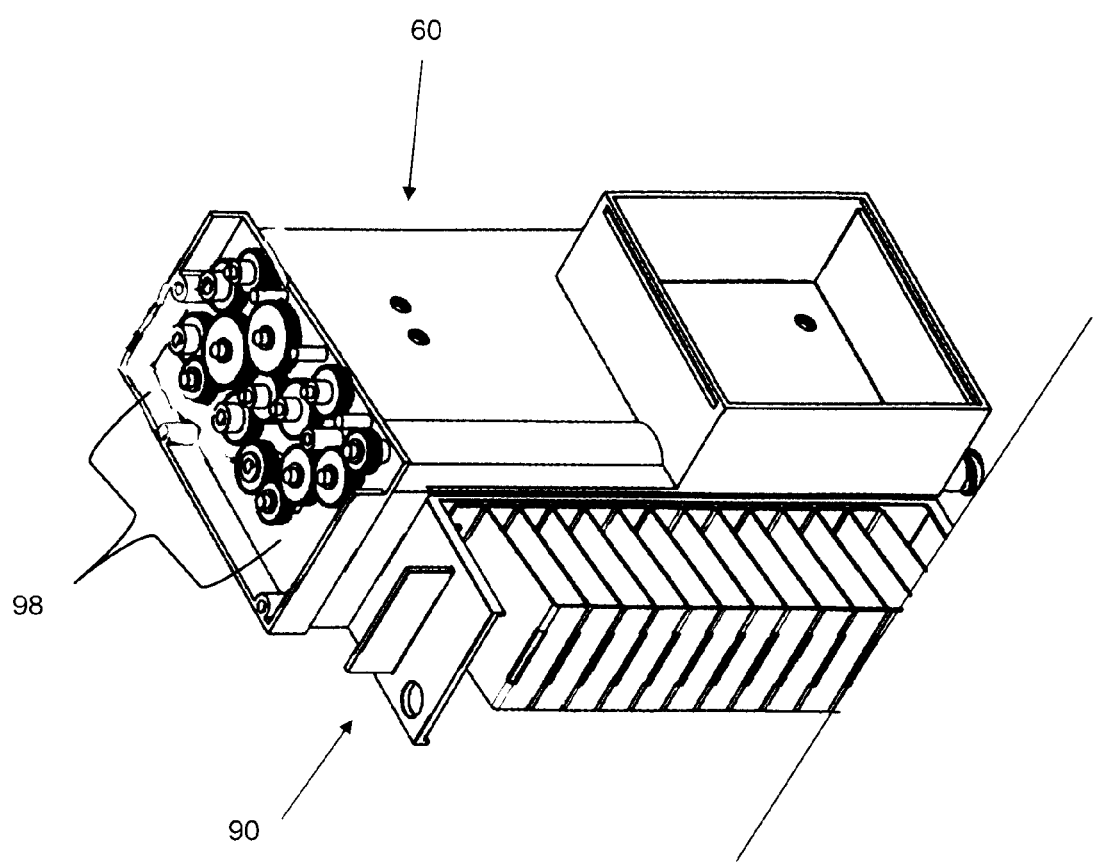
FIG. 12 depicts the drive assembly 60 attached to the detachable collection housing 90. Drive assembly gearing 98 is also shown.

In some embodiments a collection housing 90, which detaches from the drive assembly 60, includes chamber spacing 96 for positioning of sample collection chambers 26 or collection bags, vials tubes and the like. Detachment may occur by pulling the collection housing 90 away from collection needles 92, which may be non-coring or Huber needles and may removably penetrate needle housings 94. Detached drive assembly 60 and collection housing 90 are shown in FIGS. 10 and 11A-B. The needle housings 94 fluidly communicate with the sample collection chambers 26 to facilitate removal of the collection housing 90 from the drive assembly 60 while ensuring integrity of the collected sample. Referring to FIGS. 11A-B, the needle housings 94 may be provided as a single removable unit, which may be attached to the collection housing 90 by attachment to the housing top 95. Referring to FIG. 12, the collection housing 90 may then be attached to the drive assembly 60. The cooling element 44 may be positioned such that the chamber spacing 96 and thus sample collection chambers 26 are cooled. Collection needles 92 may be attached to the drive assembly base 86 or inserted into throughways 88 as shown in FIGS. 7 and 9.

Temperature control of the sample collection chamber 26 may include the presence of one or more cooling elements 44 and optionally insulation 46. In some embodiments, the sample collection chamber 26 includes a polystyrene foam layer, an insulative polymer layer, or any insulative material known in the polymer or medical device arts positioned around the circumference or perimeter of the collection chamber 26, which surrounds a collection vial, tube or bag, which is further optionally removable from the collection chamber 26. In further embodiments, a cooling element 44, including a peltier cooling element is positioned at the bottom of the chamber 26 in contact or near contact with the sample collection vial, tube or bag to assist in temperature regulation. In some embodiments, the cooling element 44 cools a chamber spacing 96 which houses a sample collection chamber 26, bag or the like. The cooling element 44 may also include a surface or substrate such as a metal surface or semi-metal surface to assist in delivery of cooling to the sample collection chamber 26. Peltier cooling elements selectively cool one end and warm an opposing end. Typically such devices operate using DC voltage and thus may be operate on a DC system or battery system. Peltier elements may be obtained from a variety of electronics suppliers. In some embodiments, a flattened collection bag extends along the cooling element to increase the cooling surface area and thus to more rapidly cool the sample as it is collected. In further embodiments an anticoagulant is preloaded into at least one of the sample collection chambers 26 or collection bag, tube, or vial.

In some embodiments, temperature is regulated at least in part using a thermosistor 27. A thermosistor 27 is a type of resistor with resistance proportional to its temperature. Accordingly, a thermosistor 27 may be used as a sensor to sense temperature. The thermosistor 27 may be positioned in contact with the collection chamber 26 or bag, in close proximity to chamber spacing 96, or along tubing such as along the primary line 12, sample collection line 18 and the like. A thermosistor 27 may be used to initiate or start a cooling element, used for continuous regulation of temperature and the like. In other embodiments, the thermosistor 27 is used to initiate a timer, such as a sample collection timer. Operation of thermosistors 27 and peltier cooling units are known in the electrical arts and can thus be employed in any suitable means such as to start, stop or alter cooling. Other regulatory sensors or elements may also be used in place of or in combination with the thermosistor 27.

In preferred embodiments fluid is primarily transported using a peristaltic pump 32 that includes a central rotor 34 with a plurality of rotor housings 68, which selectively engage the central rotor 34 and thus selectively pump along a variety of desired routes or paths while eliminating the need to provide multiple rotors 34 and corresponding pump motors 102a. Thus, by selectively engaging or joining each of the plurality of rotor housings 68 to the central rotor 34, only one pump motor 102a is required for rotor 34 operation across the entire device 10. Although not preferred, multiple pump motors 102a may be provided such as a first for delivering anticoagulant or waste and a second for sample collection.

Generally, peristaltic pumps displace fluid by selective compression of a flexible tube. More specifically, a rotor with a number of rollers or wipers rotates circumferentially. As used herein, the term "wiper" refers to any structure extending outward to compress the flexible tubing, including a roller. During rotation the rotor compresses the flexible tubing against a housing. As the rotor turns, the portion of the tube under compression closes or occludes thus forcing the fluid to move through the tube. As the tube opens to its natural state fluid flow is induced into the pump.

Figure 5:
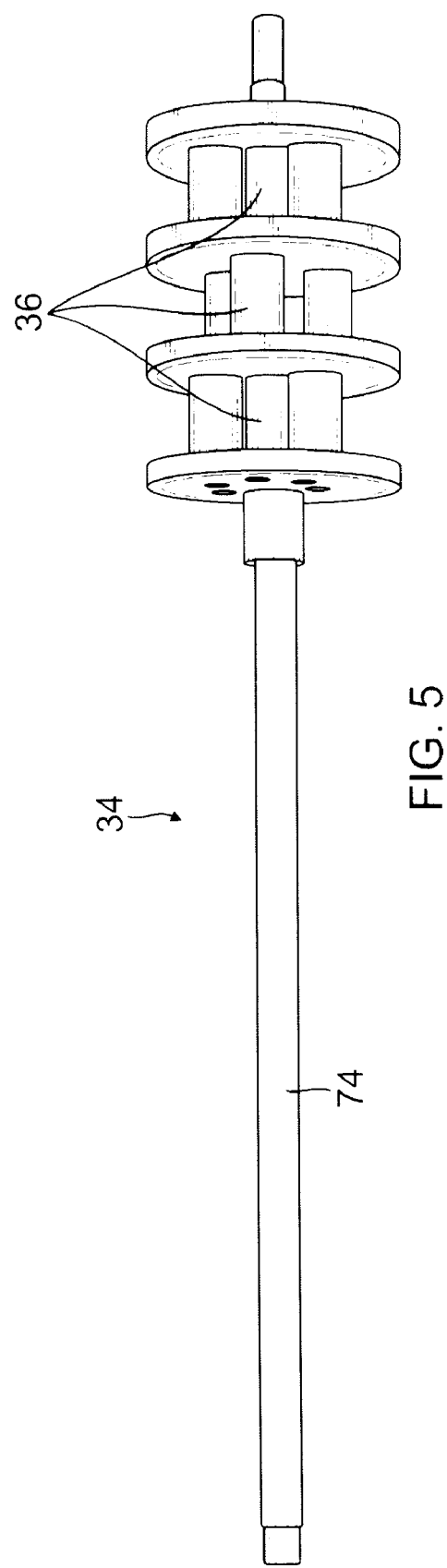
FIG. 5 depicts an exemplary central rotor 34 that includes a plurality of wipers 36 positioned along a central rod 74.

In the preferred embodiment, peristaltic pumping is selectively induced by selectively engaging rotor housings 68 individually with the central rotor 34. Most preferably, each sample collection line 28, reservoir line 18 and waste line 22 is associated with a separate or individual rotor housing 68, which can selectively be engaged. Referring to FIG. 5, the central rotor 34 may include plurality of wipers 36, which rotate in unison. The desired pumping is performed by selectively engaging the desired rotor housing 68 associated with either the fluid reservoir line 18, waste line 22, or sample collection line 28 with the central rotor 34. Referring back to FIG. 6A, these flexible tubings are each positioned along the internal surface or perimeter 78 of the rotor cavity 76, to which is inserted the rotor 34 (see FIG. 5) for engagement. As such, engagement of the rotor housing 68 with central rotor 34 compresses the associated line thus delivering fluid to the selected destination.

Figure 6B:
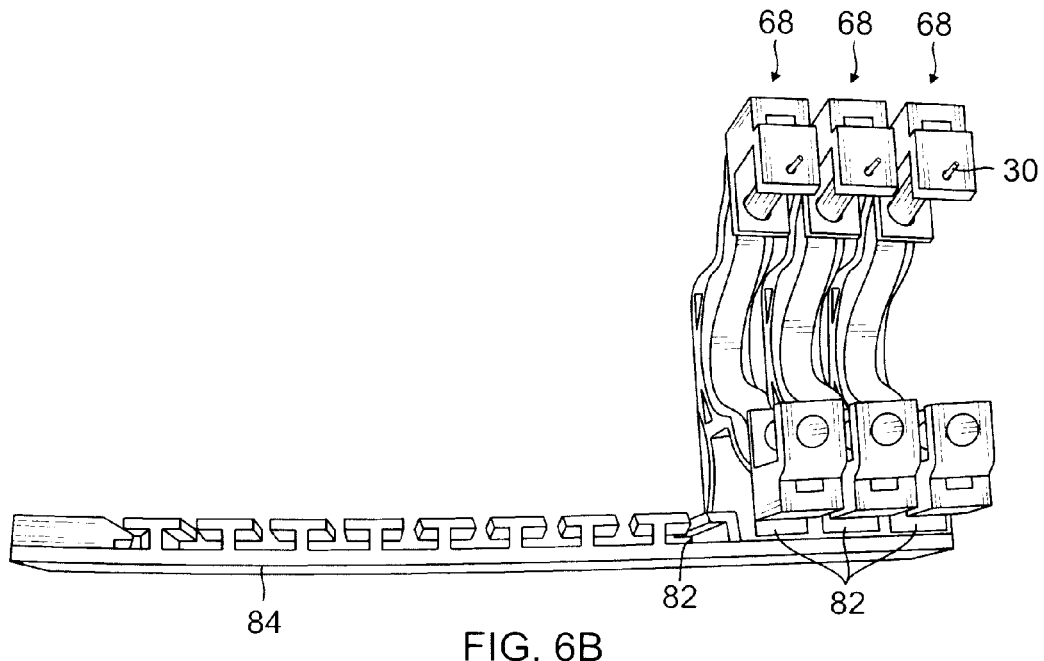
FIG. 6B depicts a plurality of rotor housings 68 horizontally aligned and slidably inserted into grooves 82 of a rotor base 84, which also shows needles 30.

In preferred embodiments rotor housings 68 are aligned horizontally and slidably attached to a rotor base 84, such as through sliding complementary surfaces including tongue 80 and groove 82 and the like. By slidably attaching the rotor housing 68 to the rotor base 84, the rotor housing 68 is permitted to slide between engaged and a disengaged positions. FIG. 15A-B provides alternative rotor housings 68 which provide sliding guides 81 to guide sliding. In other embodiments, the rotor housing 68 is pivotally engaged with the rotor base 84 to permit pivoting between engaged and disengaged configurations. In still further configurations, rotational engagement may provided. Thus, while the rotor housing 68 selectively engages the central rotor 34, a variety of configurations may be provided within the scope of the present invention and are thus nonlimiting. FIG. 6B provides an exemplary configuration showing the horizontal alignment of rotor housings 68.

Figure 3:
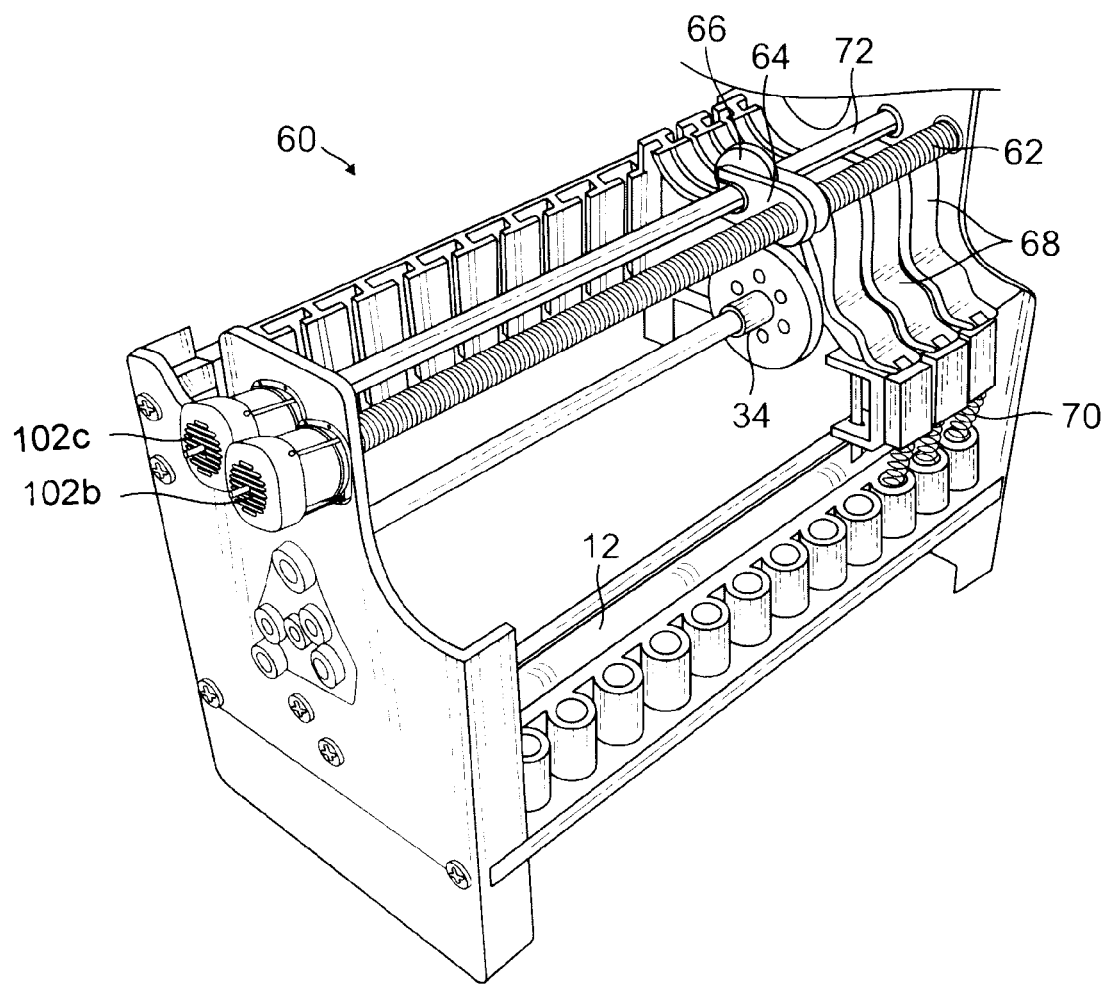
FIG. 3 provides an exemplary drive assembly 60 depicting a positioning rod 62 operably connected to a positioning motor 102b for positioning a cam assembly 64 with rotatable cam 66 along a series of rotor housings 68, which are shown disengaged from the central rotor 34. Disengagement is further evident by decompressed springs 70. A rotating rod 72 operably connected to a cam motor 102c is also shown which rotates the cam 66 towards and away from the rotor housing 68 thus selectively engaging and disengaging the rotor housing 68 from the central rotor 34.

One skilled in the present art will recognize that selective engagement of the rotor housing 68 with the central rotor 34 may occur using a variety of methodologies. In a preferred embodiment, a cam assembly 64 induces engagement of the rotor housing 68 with the central rotor 34. Most preferably the cam assembly 64 includes a rotatable cam 66 and is positioned in proximity to the desired rotor housing 68 using a threaded positioning rod 62 and positioning motor 102b. An example is shown in FIG. 3. Thus, when the rotor housings 68 are horizontally aligned, a threaded positioning rod 62 may horizontally position the cam assembly 64 by rotation through a complementary threaded aperture within the cam assembly 64. Accordingly the cam assembly 64 may be selectively positioned by instructing a positioning motor 102b to rotate the threaded positioning rod 62 either clockwise or counterclockwise until the cam assembly 64 is in proper position, such as above the desired rotor housing 68. The microprocessor 38, which is operatively connected to the positioning motor 102b, may determine the position of the cam assembly 64 by measuring rotations, activation of a position sensor and the like. Although the preferred embodiment includes a threaded positioning rod 62 complementary to a threaded aperture, any suitable positioning means may be employed, such as pushing or pulling rods, tracks and the like.

Figure 4:
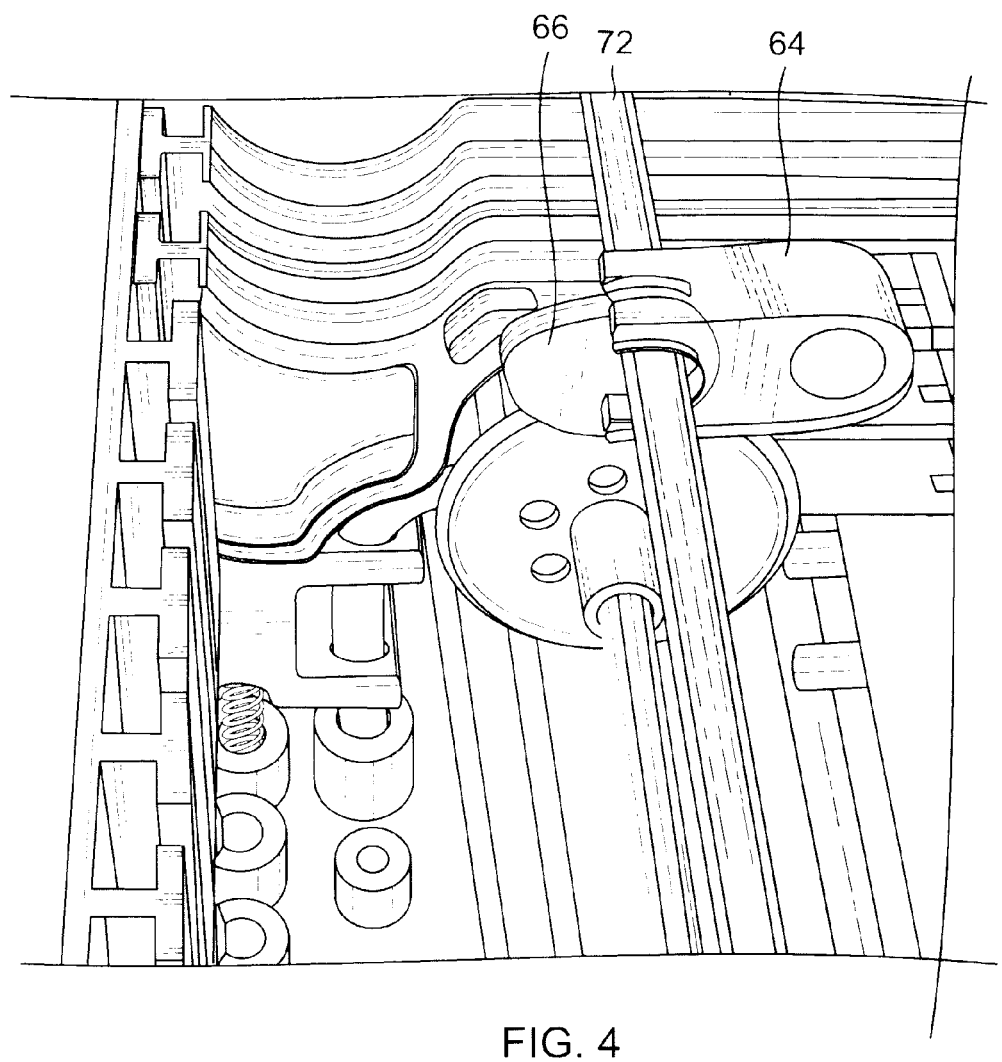
FIG. 4 depicts and exemplary cam assembly 64 having a rotatable cam 66 that is rotatably controlled by a slidably inserted rotating rod 72.

Once positioned above the desired rotor housing 68, the cam 66 may be rotated to displace the rotor housing 68 from the disengaged position or configuration to an engaged position or configuration. Most preferably, the cam 66 rotates and pushes the rotor housing 68 downward to engage the central rotor 34. The cam assembly 64 with cam 66 and cam rod 72 is shown in FIG. 4. In addition, pushing the cam 64 against the rotor housing 68 may also push the needle 30 into the primary line 12 if sample collection is desired. Rotation of the cam 66 may be accomplished by rotation of a rotating rod 72 that is slidably positioned through the cam 66. However, any configuration able to selectively press and release the rotor housing 68 for engagement and disengagement may be employed. In some embodiments, actuating arms selectively press against the rotor housing 68 and thus engage the rotor housing 68 with the central rotor 34. In other embodiments a piston configuration is provided to position a cam assembly 64 or rotate a cam 66. Such configurations may include a plurality of complementary opposing pistons that modulate in opposing directions and thus cause cam assembly 64 positioning or cam 66 rotation.

Preferably, disengagement occurs by rotating the cam 66 away from the rotor housing 68. One or more springs 70 may be provided to further assist with disengagement. In some embodiments, a spring 70 is compressed during engagement and is decompressed during disengagement to move or to assist in moving the rotor housing 68 away from the central rotor 34.

Operations including positioning of the cam assembly 64, rotating the cam 66, rotating the central rotor 34, and actuating of the selecting valve 24 may be accomplished using a variety of motors 102, which may be controlled by a microprocessor 38 operably linked to memory 40. Motors 102 that twist, switch, pivot and the like are commercially available throughout the electrical component industry and may readily obtained from a variety of electrical suppliers by those skilled in the present art. Thus, while the present invention provides specific structural examples, one skilled in the art will recognize alternative configurations may perform substantially the same operation and thus are to be encompassed with the present invention.

In preferred embodiments, motors 102 provided with the present invention are detachable from the drive assembly 60, which allows their interchangeability between multiple drive assemblies 60. In preferred embodiments the drive assembly 60 reversibly engages the motor 102 configuration. As such, the drive assembly 60 may be removed or replaced between collection events, such as between different subjects, collection time frames and the like.

Figure 13:
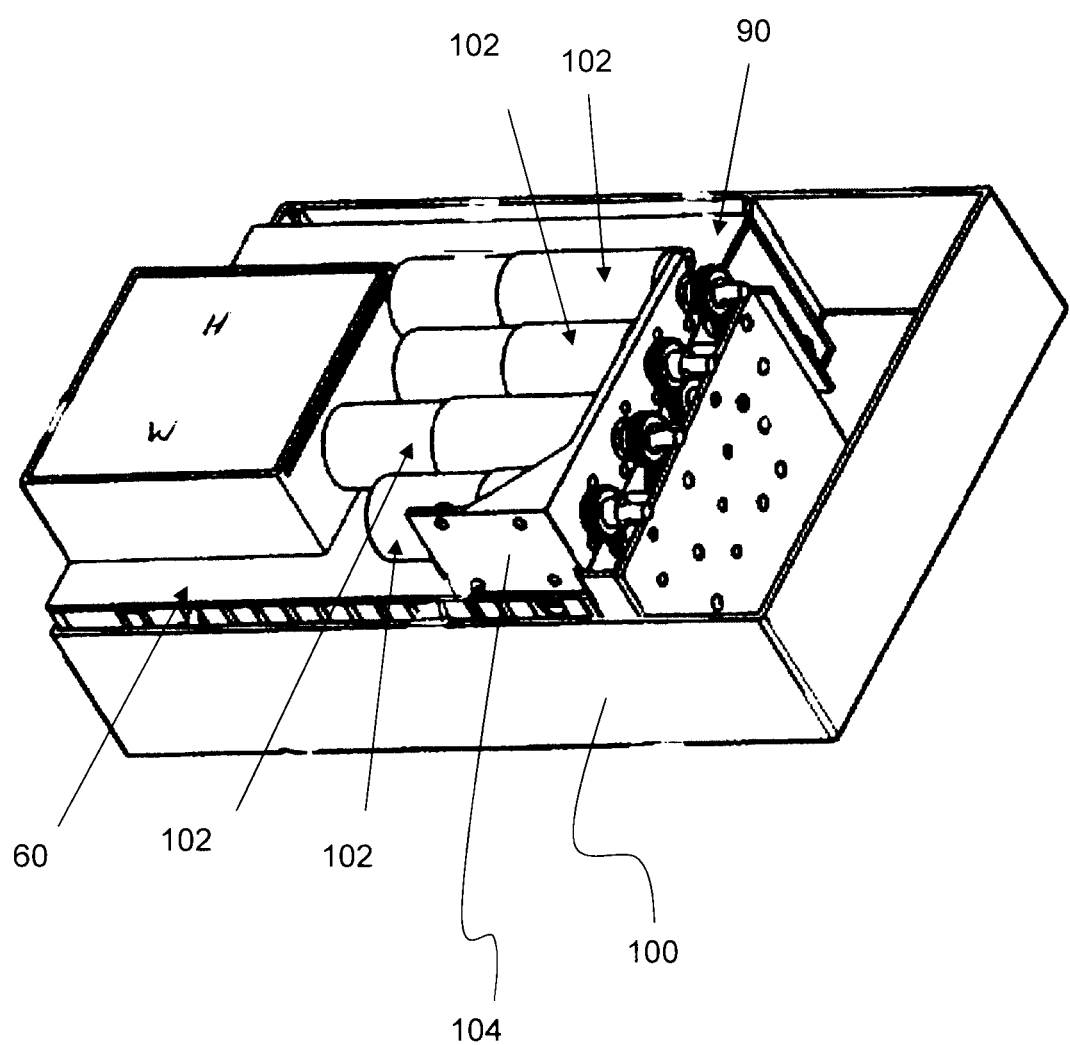
FIG. 13 depicts an instrument housing 100, which houses the motors 102 mounted to a motor mount 104 and removable drive assembly 60 and detachable collection housing 90.

Preferably, an instrument housing 100 permanently houses motors 102, such as by a motor mount 104, as shown in FIG. 13, microprocessor 38, memory 40 and the like and provides connections to operatively connect the features with the drive assembly 60. Such components may be glued or fastened in desired positions as known in the art. Upon insertion of the drive assembly 60 to the instrument housing 100, the positioning rod 72, such as a threaded rod may engage a positioning motor 102b; the central rotor rod 74 may engage the pump motor 102a; and the cam rod 66 such as an asymmetric rod may engage a cam motor 102c. In addition, a selecting valve rod 25 or structure may engage a valve motor 102d to operate the selecting valve 24. One skilled in the art will recognize engagement and disengagement of the drive assembly 60 with motors 102 may occur through a variety of structures such as complementary engaging surfaces and the like. For instance, complementary adapters may be provided for connection as known in the medical device, mechanical and electrical arts. Further, the instrument housing may include guide tracks or moulds to guide complimentary engaging structures towards one another to facilitate engagement. Thus insertion of a disposable drive assembly 60 into a reusable instrument housing 100 may result in connection of rods to motors 102, motors 102 to drive assembly gearing 98, such as rotational or positioning gears and the like to operatively connect the drive assembly 60 as shown by FIGS. 12 and 13. Further, electrical surfaces, adapters or pins may engage cooling elements, wiring, electrical connections and the like as known in the medical device and electrical arts. In some embodiments, the instrument housing 100 is adorned by the subject such as strapped via a belly band in the case of laboratory animals or joined to a belt in the case of human subjects. In other embodiments, the instrument housing 100 is remote from the animal but attached via the inlet end 14 of the primary line 12.

Activation and synchronization of device 10 operations are typically controlled by the microprocessor 38, which is operably linked to memory 40 and includes a power source, such as a battery or AC adapter. In preferred embodiments, the device 10 is programmed to perform a series of operations or collections according to a series of time points or a series of occurrences, which may be selected by the user. This information is provided to the microprocessor 38 for storage in memory 40 and retrieved as necessary. Thus, the microprocessor 38 coupled to memory 40 may keep track of time points, positioning of the cam assembly 64, rotational positioning of the cam 66, pumping operation and the like in view of operations or functions provided herein. Operations and functions may be carried out according to programmed thresholds.

In some embodiments, blood samples are collected during a series of programmed time points designated by the user. Operations such as rinsing of the primary line 12, collection of waste and the like may be preprogrammed to automatically associate with a user's selected collection regimen or may be independently chosen. Accordingly, the microprocessor 38 may be provided with automatically generated instructions for positioning of one or more cam assembles 64; rotation of one or more cams 66; selecting one or more selections from one or more selecting valves 24; rotation of the central rotor 34, whether clockwise or counterclockwise; and the like.

Thus, the microprocessor 38 instructs the activities of the moving elements such that blood may be drawn and selectively collected, while optionally optimizing conditions for collection, such as the rinsing or waste collection cycles. These functions may be performed at least in part by directing a series of motors 102 to perform their intended function. Similarly, the microprocessor 38 may activate one or more cooling elements 44, associated with one or more collection chambers 26 or collection housing 90.

Further, the microprocessor 38 may store in memory 40 a variety of data, whether stored for consideration by the end user or characteristics of operation that may optimize performance and the like. In some instances, positioning of the cam assembly 64 relative to a series of rotor housings 68 is stored in memory 40 for later access. In some instances, values associated with volumes or characteristics of the primary line 12, reservoir line 18, waste line 22, sample collection lines 26 and the like are stored. In some instances time periods are stored for collection, rinsing, waste removal and the like. Thus, time periods or speeds of rotation of the central rotor 34, positioning rod 62, cam rod 72 and the like may be stored. In some embodiments, an occlusion detection system positioned within the waste line 22 or primary line 12 is provided which may store information in memory, such as pressure, flow and the like. Thus, the memory 40 may include read-only memory (ROM) and may include random access memory (RAM) and desired by the user or a loaded software program.

The instrument housing may also provide an interface 42, such as a display to selectively view the status, indicated parameters, facilitate entry of instructions and the like. Occlusion alarms, battery levels, and like may also be provided. Similarly, the housing may provide operational buttons, switches, knobs as desired to facilitate data entry to program or to alter programming; however, in preferred embodiments alarms and control mechanisms that alarm or are controlled by the user are remote from the instrument itself.

The device 10 may be programmed and progress monitored remotely using an external control unit. The external control unit may take a variety of forms such as a hand held instrument programmed for entry of data options, a computer, such as a laptop computer or desktop computer, a PDA, a mobile phone and the like. Thus a variety of displays, keyboards, printers, storage media and network systems are also encompassed within the present invention. One skilled in the present art will recognize that the external control unit may operably connect or communicate with the microprocessor using a variety of suitable communication means such as through wired communication, wireless communication or a mixture thereof. Such communication methods are well known in the computer and medical device arts and may include electrically operably computer ports, transmitters, receivers and the like. Thus, technologies such as WI-FI and Bluetooth communication as well as others are encompassed by the present invention. Although wireless operation may be preferred while monitoring operation, wired communication may be preferable during setup to reduce discharge of instrument batteries. Further, wired communication may also provide a charging source for rechargeable batteries.

Preferably, the external control unit is loaded with software that allows the user to select from menus or listings of available options. In some embodiments, custom entries, timelines and the like may be entered by the user. Thus, a preprogrammed library of information may be provided as well as the ability to generated new library entries or custom operations. Such programs may be generated by those skilled in the medical device and computer programming arts. In some embodiments, identifiers such as a collection tube identifier and primary line identifier are preprogrammed such that the user may select the desired entry from a listing of identifiers. In other embodiments, a scanner may detect a label associated with such device, such as a bar code. Thus once selected the identifier may include a group of instructions or parameters preloaded for transfer as operating instructions for the device 10. As such characteristics such as cavity 50 volume and sample collection chamber 26 volume may be automatically chosen and programmed by the software according to user chosen options.

In various embodiments, the software permits the user to choose the number of samples to be collected, time periods over which collection occurs and the like. The programming may prescribe thresholds for detection or as desired by the user. Various alarms such as occlusion, low battery, temperature, timing and the like may also be provided. On skilled in the art will recognize such programming may include any identifiers known in the art for sample identification, time point designation and the like. Data may be exported into a variety of formats as desired by the user such as spreadsheets, graphical presentations, word editing formats and the like. Thus the software may export files to programs offered by Microsoft, Adobe, Corel and the like as known in the art.

The invention has been described in an illustrative manner to assist readers in constructing and using the device, instrument, systems and methods and thus should not be limited to any particular structure when additional examples or guidance has been provided. Unless specifically provided, one skilled in the present art will be able to obtain, construct or assemble the various components discussed above using materials and methods known in the art in view of the guidance provided. Materials such as polypropylene, polystyrene, polymer plastics, metals, semi-metals, metal alloys and the like may be formed, injection moulded, bent, glued, joined and like as known in the medical device arts. Electrical communication such as through wires, leads, circuit boards and the like can be joined to affect function as known by those with ordinary skill in the electrical and computer arts.

What is claimed is:

1. A drive assembly with collection chambers for sampling biological fluids comprising:
   a) a primary line having an inner cavity surrounded by a wall, said primary line comprising an an inlet end capable of receiving a biological fluid;
   b) a fluid reservoir;
   c) a waste container;
   d) a plurality of sample collection chambers;
   e) a peristaltic pump comprising a central rotor and a plurality of rotor housings, each capable of selective engagement with said central rotor, wherein each rotor housing comprises a sample collection line positioned along an inner perimeter and fluidly connected at one end to one of said plurality of collection chambers and at an opposing end to one of a plurality of needles, further wherein said engagement compresses said sample collection line against said central rotor and drives said needle into said inner cavity of said primary line; and
   f) a cam assembly comprising a rotatable earn, positionable along said plurality of rotor housings, wherein rotation of said cam in a first position selectively engages one of said rotor housings with said central rotor and rotation in a second position releases said rotor housing from engagement with said central rotor.

2. The drive assembly according to claim 1, wherein said plurality of collection chambers each comprise a peltier cooling element.

3. The drive assembly according to claim 2, further comprising a reversibly attachable collection housing that houses said plurality of collection chambers, wherein each of said plurality of collection chambers each house a collection vial, tube or bag, further wherein said collection chambers are insulated.

4. The drive assembly according to claim 1, further comprising a threaded positioning rod complementary to a threaded aperture extending through said cam assembly, wherein rotation of said threaded positioning rod horizontally positions said cam assembly across and above said plurality of rotor housings.

5. The device according to claim 4, further comprising a rotating shaft slidably inserted through said cam, wherein rotation of said shaft rotates said cam into said first and second positions.

6. The device according to claim 4, further comprising a selecting valve for selecting communication between said primary line and said fluid reservoir, said primary line and said waste container, or said fluid reservoir and said waste container.

7. The device according to claim 4, further comprising a plurality of springs contacting said plurality of rotor housings, wherein at least one spring is compressed when said cam is in said first position and decompressed when in said second position.

8. A instrument for sampling a biological fluid comprising:
   a) the drive assembly according to claim 1; and
   b) an instrument housing, comprising:
      i) a peristaltic pump motor that rotates said central rotor,
      ii) a positioning motor for positioning said cam assembly,
      iii) a cam motor for rotating said cam between said first position and said second position, and
      iv) a microprocessor with memory and capable of connection to a power source, wherein said microprocessor instructs operation of said pump motor, positioning motor and cam motor.

9. The instrument according to claim 8, wherein said drive assembly is reversibly housed within said instrument housing and reversibly attachable to said peristaltic pump motor, positioning motor, and cam motor.

10. The instrument according to claim 9, wherein said instrument housing further comprises a peltier cooling element for cooling said collection chambers.

11. The instrument according to claim 10, further comprising a thermosistor.

12. The instrument according to claim 9, wherein,
   a) said drive assembly further comprises:
      i) a threaded positioning rod complementary to a threaded aperture extending through said cam assembly, wherein rotation of said threaded positioning rod horizontally positions said cam assembly across said plurality of rotor housings,
      ii) a rotating shaft slidably inserted through said cam, wherein rotation of said shaft rotates said cam into said first and second positions,
      iii) a plurality of springs associated with said plurality of rotor housings, wherein at least one spring is compressed when said cam is in said first position and decompressed when in said second position;
   b) said positioning motor rotates said threaded positioning rod; and
   c) said cam motor rotates said rotating shaft.

13. The instrument according to claim 12, wherein,
   a) said drive assembly further comprises a selecting valve for selecting fluid communication between each of said primary line and said fluid reservoir, said primary line and said waste container and said fluid reservoir and said waste container; and
   b) said instrument housing further comprises a valve motor for operating said selecting valve.

14. A system for sampling a biological fluid comprising:
   a) the instrument according to claim 13; and
   b) an external control unit operably linked to said microprocessor, wherein said external control unit comprises a computer system comprising a software program, wherein said software program accepts entry of data corresponding to said a sample volume for collection into each of said collection chambers and a number of sample volumes for collection;
   wherein said external control unit determines an order of sample collection and rinsing, and transfers said order as instructions to said microprocessor.

15. The device according to claim 1, wherein said plurality of needles remain recessed in said wall of said primary line when said rotor housings are not engaged.

* * * * *